United States Patent [19]

Billeb et al.

[11] Patent Number: 5,446,190
[45] Date of Patent: Aug. 29, 1995

[54] PROCESS FOR THE PREPARATION OF ALKYL FLUOROBENZOATES IN HIGH PURITY AND HIGH YIELD

[75] Inventors: Gilbert Billeb, Kelkheim; Wolfgang Tronich, Eppstein, both of Germany

[73] Assignee: Hoechst Aktiengesellschaft, Frankfurt, Germany

[21] Appl. No.: 339,761

[22] Filed: Nov. 15, 1994

[30] Foreign Application Priority Data

Nov. 17, 1993 [DE] Germany .................. 43 39 208.3

[51] Int. Cl.$^6$ ............................................. C07C 69/76
[52] U.S. Cl. ................................................... 560/103
[58] Field of Search ........................................ 560/103

[56] References Cited

U.S. PATENT DOCUMENTS

| | | | |
|---|---|---|---|
| 3,223,725 | 12/1965 | Hill | 560/103 |
| 3,317,569 | 5/1967 | Larsen et al. | 560/103 |
| 3,579,577 | 5/1971 | Hoch | 560/103 |
| 3,703,546 | 11/1972 | Leaper et al. | 560/103 |
| 4,985,588 | 1/1991 | Kumai et al. | 560/103 |
| 5,292,928 | 3/1994 | Miltenberger | 560/103 |

FOREIGN PATENT DOCUMENTS

| | | |
|---|---|---|
| 3267745 | 4/1988 | Japan . |
| 63-267745 | 11/1988 | Japan . |
| 50039233 | 2/1993 | Japan . |

*Primary Examiner*—Paul J. Killos
*Attorney, Agent, or Firm*—Connolly & Hutz

[57] ABSTRACT

Process for the preparation of alcohol fluorobenzoates of the formula (I)

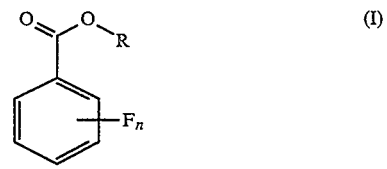

in which R is an alkyl radical and $F_n$ is 1 to 4 fluorine atoms which, independently of one another, are bonded to the aromatic ring, by reacting a fluorobenzyl chloride of the formula (II)

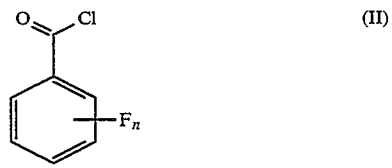

in which $F_n$ is as defined above, with an at least stoichiometric amount of an alkali metal alcoholate ROM in which R is as defined above and M is an alkali metal from the group consisting of Li, Na and K, in the corresponding alcohol ROH at temperatures from $-10°$ C. to 150° C., the solvent is distilled off, if appropriate, and the alkali metal chloride formed is separated off by treating the mixture with water or by filtration.

17 Claims, No Drawings

PROCESS FOR THE PREPARATION OF ALKYL FLUOROBENZOATES IN HIGH PURITY AND HIGH YIELD

Alkyl fluorobenzoates of the formula (I) are important intermediates for the preparation of pharmaceuticals and crop protection products.

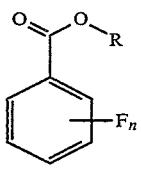
(I)

Some processes for the preparation of such esters are described in the literature. For example, ethyl 3-fluorobenzoate and methyl 3-fluorobenzoate are obtained from the silver salt of the acid (Paterno et al., Gazz. Chim. Ital. 12, 90). However, this process is, at best, suitable for the preparation of quantities on a bench scale since it involves the use of an expensive silver salt.

Ethyl 4-fluorobenzoate and the corresponding methyl ester are formed when 4-fluorobenzoic acid is reacted with ethanol or methanol, respectively, while passing in hydrogen chloride gas (Schmitt et al., J. Prakt. Chem. 1 (2), 400; Bacon et al., J. Org. Chem. 3, 281 (1938); Bowden et al., H. Chem. Soc. 1940, 1249). This reaction involves long reaction times, yet only moderate yields and is, moreover, disadvantageous since alkyl halides are formed as a side reaction because hydrogen chloride gas reacts with the alcohols (cf. Example 1).

Methyl 2- and 4-fluorobenzoate and ethyl 2- and 4-fluorobenzoate are furthermore obtained by heating 2- or 4-methoxycarbonylphenyldiazonium tetrafluoroborate (Bergmann et al., Chem. Ber. 64, 1455 (1931); Schiemann et al., Org. Synth. Coll. Vol. II, 299 (1943); Japanese Patent 05039233). Since the starting substances required for this process are complicated to prepare, these reactions cannot be carried out easily from the technological point of view and, moreover, frequently give only moderate yields.

Variants of this reaction, which are only suitable for bench-scale quantities, are the reaction of ethyl nitrite with 4-aminobenzoic acid/ethyl hexafluorosilicate (Wiley et al., J. Am. Chem. Soc. 71, 1863 (1949)) and the reaction of methyl 2-aminobenzoate with nitrosonium tetrafluoroborate (Milner et al., Synth. Commun. 22 (1), 73 (1992)).

Methyl 4-fluorobenzoate can also be prepared by Pd-catalysed alkoxycarbonylation of 4-iodofluorobenzene, which is not available at a reasonable price on an industrial scale (Carpentier et al., Tetrahedron Lett. 32 (36), 4705 (1991)). However, this process gives approximately 9% of methyl 4-methoxybenzoate as a by-product. Variants of this reaction are the reactions of 4-iodofluorobenzene with ethanol and CO on zeolite catalysts or with Pd catalysis, but these reactions give yields of only 62 and 76%, respectively (JP 04046139; JP 03197441), and the reaction of 4-fluorobromobenzene with methyl iodide and CO on cobalt catalysts (Itoh et al., Mol. Catal. 48 (1), 11 (1988)).

Suitable preparative methods for alkyl fluorobenzoate on a bench scale only are the electrochemical reduction of 2,6-difluorobenzoic esters (Hebri et al., Synth. Commun. 21 (22), 2377 (1991)) and the anodic oxidation of 4 - fluorobenzoyloxyacetic acid (4-F-$C_6H_4$COOCH$_2$COOH) (Thomas et al., Chem. Ber. 118 (7), 2777 (1985)).

Processes for the preparation of alkyl 4-fluorobenzoates by reacting the corresponding fluorobenzoyl chlorides with alcohols are also described in the literature (FR 2541282; Smith et al., J. Am. Chem. Soc. 79, 875 (1957); Spratt et al., Anal. Chem. 56 (12), 2038 (1984)). However, this reaction generally involves the formation of alkyl chloride as a side reaction (cf. Example 1), which reduces the yield and results in waste air which is ecologically hazardous. Moreover, this reaction frequently proceeds slowly and requires elevated temperatures, which additionally favor the formation of alkyl chloride. While the use of amines as solvents as catalysts, as described in these references, accelerates the reaction, it is disadvantageous from the technological point of view since amine hydrochlorides are formed from the amine and the hydrochloric acid which is produced. Regeneration of the hydrochlorides to the free amine would be complicated. In addition, the product quality in this case is generally so poor, that it requires complicated working-up by distillation (cf. Example 2).

There was therefore a very pressing need for a novel process for the preparation of alkyl fluorobenzoates which does not have the above-described shortcomings, uses readily accessible substances as starting materials, makes accessible the desired compounds in high yield, and from the technical point of view can furthermore be carried out without complex procedures.

The solution for achieving this object is a process for the preparation of alkyl fluorobenzoates of the formula (I)

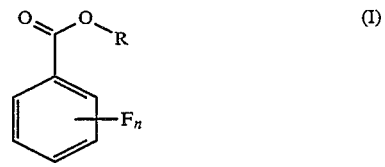
(I)

in which R is an alkyl radical and $F_n$ is 1 to 4 fluorine atoms which, independently of one another, are bonded to the aromatic ring, by reacting a fluorobenzoyl chloride of the formula II

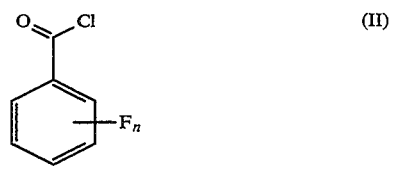
(II)

in which $F_n$ is as defined above, with an at least stoichiometric amount of an alkali metal alcoholate ROM in which R is as defined above and M is an alkali metal from the group consisting of Li, Na and K, in the corresponding alcohol ROH at temperatures from −10° C. to 150° C., the solvent is distilled off, if appropriate, and the alkali metal chloride formed is separated off by treating the mixture with water or by filtration.

Expediently, the reaction is carried out in such a way that 1.0 to 5.0 mol, in particular 1.0 to 3.0, preferably 1.0 to 1.5 mol, of alcoholate are employed per mol of acid chloride to be reacted. This is advantageously introduced dissolved in such an amount of the corresponding alcohol that the alcoholate content of the solution is between 1 and 60%, in particular 10 to 50%, preferably between 20 and 40%. The acid chloride is added dropwise, if appropriate with cooling, at a temperature of −10° C. to boiling point of the alcohol, in particular 10° C. to boiling point of the alcohol. Then, stirring is continued at −10° C. to reflux temperature of the alcohol, in particular 10° C. to reflux temperature of the alcohol, preferably at 10° C. to 40° C. In many cases, it has proved advantageous to dilute the reaction mixture with water and to isolate the product by phase separation or filtration. A procedure in which excess alcohol is distilled off before water is added has proved expedient.

A further possibility is isolation of the product by filtering off the alkali metal salt and subsequently separating off the alcohol by distillation. Thus, the present process is distinguished from the processes known from the literature by high yields, high purities being achieved without purification of the crude products. It is particularly surprising in this process that the feared nucleophilic fluorine/methoxy exchange, as it is described, for example, by Williams et al., J. Org. Chem. 42., 3414 (1977), James et al., J. Fluorine Chem. 27 (N1), 91 (1985) and in many other references, is not observed. Nor are alkyl halides formed in this process, so that the purification of the waste air does not require any specific procedures. The starting materials are inexpensive and available in industrial-scale quantities. 3-Fluorobenzoyl chloride is prepared, for example, by side-chain chlorination of 3-fluorotoluene followed by hydrolysis, or by reaction of 3-fluorobenzoic acid with thionyl chloride. The space-time yields are high at all levels.

The examples which follow are intended to illustrate the process without limiting it thereto.

EXAMPLES

The fluorobenzoyl chlorides used for the comparison examples were prepared by side-chain chlorination of the corresponding fluorotoluenes followed by hydrolysis.

Example 1 (comparison example):

Reaction of alcohols with 3-fluorobenzoyl chloride a) 600.0 g (3.78 mol) of 3-fluorobenzoyl chloride are introduced into the reaction vessel at room temperature. 130.0 g (4.06 mol) of methanol are added dropwise in the course of 3 hours, the temperature being held at 30° C. by means of cooling. After approximately 15 minutes, the evolution of hydrogen chloride started. While the methanol is metered in, >10% by volume of methyl chloride are detected in the waste gas by gas chromatography. After all the methanol has been metered in, stirring is continued for 15 minutes at 30° C. and then for 30 minutes at reflux temperature to achieve a complete reaction. Excess methanol and dissolved hydrochloric acid are then distilled off. Yield: 537.1 g (3.48 mol) of methyl 3-fluorobenzoate=92.2% of theory.

b) 638.0 g (4.02 mol) of 3-fluorobenzoyl chloride are introduced into the reaction vessel at room temperature. 195.0 g (4.22 mol) of ethanol are added dropwise in the course of 2 hours, during which process the temperature rises to 52° C. After approximately 15 minutes, the evolution of hydrogen chloride starts. While the ethanol is metered in, >0.5% by volume of ethyl chloride can be detected in the waste gas. Stirring is subsequently continued for 12 hours at 55° C., without a complete reaction of acid chloride being achieved. After a further 2 hours at 95° C., the reaction is quantitative. Excess alcohol and hydrogen chloride are removed by distillation in vacuo at 40° C. Yield: 642.1 g (3.82 mol) of ethyl 3-fluorobenzoate=95% of theory.

c) In further experiments, methanol and ethanol, respectively, are introduced into the reaction vessel, and the acid chloride is metered in, and temperatures and reaction times are varied, and a formation of methyl chloride and ethyl chloride, respectively, was always observed. The yield is not improved.

Example 2 (comparison example):

Reaction in the presence of tributyl amine 112.0 g (3.5 mol) of methanol and 583.0 g (3.15 mol) of tri-n-butylamine are introduced at room temperature. 500.0 g (3.15 mol) of 3-fluorobenzoyl chloride are added dropwise at room temperature in the course of 2 hours. No waste gas is observed. After all the 3-fluorobenzoyl chloride has been metered in, stirring is continued for 20 minutes at 80° C. After this time, the reaction is quantitative. The batch is diluted with 1500 ml of water and 100 ml of concentrated HCl. The organic phase is separated off and washed until neutral using 100 ml of water. Yield: 468.2 g of crude methyl 3-fluorobenzoate (=88.2% of theory, calc. as 100%) containing 91.5% of pure substance and 6.4% of tributylamine. 600 g of hydrous tributylamine are recovered by rendering the aqueous phase alkaline and subsequently separating the phases, but this tributylamine has to be dried first before it is used in further experiments.

Example 3:

Reaction of sodium methylate with 3-fluorobenzoyl chloride a) 1427 g (7.66 mol) of a 29% solution of sodium methanolate in methanol are introduced into the reaction vessel at room temperature, and 1200 g (7.56 mol) of 3-fluorobenzoyl chloride are added dropwise in the course of 3 hours, during which process the temperature is kept at room temperature by means of cooling. A colorless suspension of crystals is formed. No waste gas is observed. The methyl chloride content of the gaseous space of the flask is far below 0.1% by volume. Stirring is continued for 30 minutes at room temperature. After this time, the reaction was quantitative. Excess methanol is subsequently distilled off under atmospheric pressure, and 1500 g of water are added to the bottom product which remains. The organic product phase is separated off. Yield: 1131 g (7.33 mol) of methyl 3-fluorobenzoate=97% of theory. Pure substance content: 99.9% (GC, organic constituents), water content 0.5%.

b) An analogous experiment at reflux temperature gave the same results.

Examples 4 to 9:

Other reactions

The following reactions were carried out analogously to Example 3a):

Example 4:

The reaction of 3-fluorobenzoyl chloride with sodium ethanolate in ethanol analogously to Example 3a) gives a yield of 97% of theory at a pure substance content of 99.8% (GC), water content 0.4%.

Example 5:

The reaction of 3-fluorobenzoyl chloride with sodium n-propanolate in n-propanol analogously to Example 3a) gives a yield of 97% of theory at a pure substance content of 99.8% (GC), water content 0.5%.

Example 6:

The reaction of 3-fluorobenzoyl chloride with sodium i-propanolate in i-propanol analogously to Example 3a) gives a yield of 96% of theory at a pure substance content of 99.7% (GC), water content 0.5%.

Example 7:

The reaction of 4-fluorobenzoyl chloride with sodium methanolate in methanol analogously to Example 3a) gives a yield of 97% of theory at a pure substance content of 99.8% (GC), water content 0.4%.

Example 8:

The reaction of 3-fluorobenzoyl chloride with sodium methanolate in methanol is carried out analogously to Example 3a), but the sodium chloride is filtered off before the excess alcohol is separated off. After the alcohol is separated off, the product is obtained in the same quantity and quality.

Example 9:

The reaction of 2,6-diflurobenzoyl chloride with sodium methanolate in methanol analogously to Example 3a) gives a yield of 94% of theory at a pure substance content of 99.7% (GC), water content 0.5%.

Example 10:

The reaction of 2,4-diflurobenzoyl chloride with sodium methanolate in methanol analogously to Example 3a) gives a yield of 96% of theory at a pure substance content of 99.5% (GC), water content 0.6%.

We claim:

1. A process for the preparation of alkyl fluorobenzoates of the formula (I)

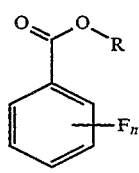
(I)

in which R is an alkyl radical and $F_n$ is 1 to 4 fluorine atoms which, independently of one another, are bonded to the aromatic ring, which comprises the steps of:

reacting a fluorobenzoyl chloride of the formula (II)

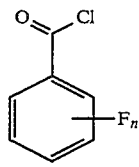
(II)

in which $F_n$ is as defined above, in a mixture with an at least stoichiometric amount of an alkali metal alcoholate ROM, in which R is as defined above and M is an alkali metal from the group consisting of Li, Na and K, in the corresponding alcohol ROH having a boiling point, said reaction being conducted at temperatures from $-10°$ C. to $150°$ C., and separating off the alkali metal chloride formed.

2. The process as claimed in claim 1, wherein R is methyl, ethyl, n-propyl or i-propyl.

3. The process as claimed in claim 1, wherein $F_n$ is 1 or 2 fluorine atoms.

4. The process as claimed in claim 1, which additionally comprises the step of introducing the alkali metal alcoholate ROM into the alcohol ROH and dropwise adding the acid chloride at temperatures from $-10°$ C. to the boiling point of the alcohol.

5. The process as claimed in claim 1, wherein the concentration of the alkali metal alcoholate in the alcohol is 1 to 60% by weight.

6. The process as claimed in claim 1, wherein 1.0 to 5.0 mol of alcoholate are employed per mol of acid chloride.

7. The process as claimed in claim 1, wherein mixture is stirred.

8. The process as claimed in claim 1, which additionally comprises the steps of diluting the mixture with water and isolating the product by phase separation.

9. The process as claimed in claim 1 wherein excess alcohol is distilled off before water is added.

10. The process as claimed in claim 1, wherein the product is isolated by filtering off the alkali metal salt and subsequent removal of the alcohol by distillation.

11. The process as claimed in claim 1, wherein the solvent is distilled off while the reaction is being conducted.

12. The process as claimed in claim 1, wherein the alkali metal chloride is separated off by treating the mixture with water or by filtration.

13. The process as claimed in claim 1, which additionally comprises the step of introducing the alkali metal alcoholate ROM into the alcohol ROH and dropwise adding the acid chloride at temperatures from $+10°$ C. to the boiling point of the alcohol.

14. The process as claimed in claim 1, wherein the concentration of alkali metal alcoholate in the alcohol is 10 to 50 % by weight.

15. The process as claimed in claim 1, wherein the concentration of alkali metal alcoholate in the alcohol is from 20 to 40% by weight.

16. The process as claimed in claim 1, wherein 1.0 to 3.0 mol of alcoholate are employed per mol of acid chloride.

17. The process as claimed in claim 1, wherein 1.0 to 1.5 mol of alcoholate are employed per mol of acid chloride.

* * * * *